United States Patent
Sapir et al.

(10) Patent No.: US 7,846,742 B2
(45) Date of Patent: Dec. 7, 2010

(54) METHOD FOR DETECTING SUBSTANCE TO BE DETECTED CONTAINING AT LEAST ONE COMPONENT THAT IS DISPERSIBLE IN AIR IN THE FORM OF SOLID PARTICLES

(75) Inventors: Oren Sapir, Roissy-En-Brie (FR); Zamir Eldar, Amsterdam (NL); Abraham Bar Yoseph, Kokhav Yair (IL)

(73) Assignee: ICTS Europe Holdings B.V., Amsterdam (NL)

( * ) Notice: Subject to any disclaimer, the term of this patent is extended or adjusted under 35 U.S.C. 154(b) by 781 days.

(21) Appl. No.: 10/677,225

(22) Filed: Oct. 3, 2003

(65) Prior Publication Data
US 2004/0202574 A1  Oct. 14, 2004

(30) Foreign Application Priority Data
Apr. 8, 2003  (FR)  ................... 03 04330

(51) Int. Cl.
*G01N 33/00* (2006.01)
(52) U.S. Cl. ............................ 436/177; 422/83; 422/88; 422/94
(58) Field of Classification Search .................. 422/83, 422/88, 94; 436/177
See application file for complete search history.

(56) References Cited

U.S. PATENT DOCUMENTS 3,826,067 A * 7/1974 Wilder et al. ................. 55/524
4,818,870 A  4/1989 Griffiths
5,859,362 A  1/1999 Neudorfl
6,073,499 A * 6/2000 Settles ...................... 73/864.81
6,642,513 B1 * 11/2003 Jenkins et al. .............. 250/288

FOREIGN PATENT DOCUMENTS

EP  0169057  1/1986

OTHER PUBLICATIONS

Database WPI, Section Ch, Week 200215, Derwent Publications, Ltd., London GB; Class B04, AN 2002-112284 XP002269034 & NL 1 014 458, Duinmeijer, Aug. 24, 2001.
Miniaturized Explosives Preconcentrators for Use In Man-Portable Explosives Detection Systems, Hammum et al, International Carnahan Conference 2000, Canada, vol. 34, Conf. 34, Oct. 23, 2000 pp. 222-2227, XP000994041.

* cited by examiner

*Primary Examiner*—Sam P Siefke
(74) *Attorney, Agent, or Firm*—Antonelli, Terry, Stout & Kraus, LLP.

(57) ABSTRACT

The invention relates to a method and apparatus for detecting substance to be detected. The apparatus comprises at least one sampling member for sampling air contained in a closed space, the sampling member comprising at least one filter presenting pore or mesh size adapted to filtering solid particles of the substance to be detected that might be dispersed in the air contained in the closed space; the apparatus further comprising a pump (not shown) enabling the air contained in the closed space to be sucked in. The invention can be used for detecting a substance to be detected comprising, for example, an explosive or a narcotic.

17 Claims, 3 Drawing Sheets

METHOD FOR DETECTING SUBSTANCE TO BE DETECTED CONTAINING AT LEAST ONE COMPONENT THAT IS DISPERSIBLE IN AIR IN THE FORM OF SOLID PARTICLES

The present invention relates essentially to a method and apparatus for detecting substance to be detected containing at least one component that is dispersible in air in the form of solid particles, such as an explosive or a narcotic.

STATE OF THE ART

Until now, detecting substance containing at least one component that is dispersible in air in the form of solid particles, such as explosive, in particular plastrite (a military plastic explosive), hexogen (RDX), dynamite, PETN, TNT, or the explosion known as "watergel", or a narcotic, e.g. heroin, cocaine, Ecstasy, cannabis, marijuana, or hashish is performed empirically, in particular by sniffing with the help of a dog specially trained in using its sense of smell to detect traces of particles of said explosive or of said narcotic.

OBJECT OF THE INVENTION

A main object of the invention is to resolve the novel technical problem consisting in supplying a method and apparatus for detecting substance to be detected containing at least one component that is dispersible in air in the form of solid particles making it possible to have a rationalized detection procedure, and making it possible to process the ever-increasing quantity of loads that might contain substance to be detected passing through transit locations, in particular international transit locations such as an airport, a rail or road station, a sea port, whether carried by passengers, or in their baggage, or as freight.

Another object of the invention is to resolve this novel technical problem by a procedure which is reliable and reproducible, easy to implement, and low in cost, while making it possible in a minimum amount of time to process as many loads as it is deemed necessary to subject to inspection because they might contain substance to be detected.

For the first time, the invention makes it possible to solve all of these technical problems in a manner that is simple, safe, and reliable, that can be used on an industrial scale, and that leads to an improvement in safety and in countering international trafficking, in particular of narcotics.

DESCRIPTION OF THE INVENTION

In a first aspect, the present invention provides a method of detecting a substance to be detected containing at least one component that is dispersible in air in the form of solid particles, such as an explosive or a narcotic, for example heroin, cocaine, etc., the method comprising the following steps:

a) when a load that might contain said substance to be detected is not itself contained in a substantially closed space, placing said load in a closed space, for example by placing it in a wrapping that is substantially hermetically closed, at least for a predetermined storage time for allowing solid particles of said substance to be detected to disperse in air;

b) inserting at least one sampling member for sampling the air contained inside said closed space, at least after said load has been stored for said predetermined time in said closed space, said sampling member comprising at least one filter presenting pore or mesh size adapted to filtering solid particles of said substance to be detected that might be dispersed in the air contained in said closed space;

c) sucking in the air contained in said closed space via said sampling member containing said filter for a period of time necessary for filtering a sufficient quantity of air that might contain solid particles of said substance dispersed in said air;

d) removing the filter from the sampling member and optionally placing it in a hermetically closed receptacle prior to performing detection; and e) proceeding to detect the presence, if any, of solid particles of substance to be detected retained on said filter.

In an advantageous variant implementation, solid particles of substance to be detected present on said filter are detected by performing analysis in an analysis device adapted to detecting traces of solid particles of substance to be detected, or in a biosensor device. The term "biosensor device" is used to mean a device that is also capable of detecting an odor generated by the traces of solid particles of said substance to be detected.

In another variant implementation, the presence, if any, of traces of substance to be detected is detected with the help of a biosensor device, e.g. comprising an animal, preferably with the help of a dog specially trained for detecting the smell of traces of solid particles of substance to be detected retained on said filter, by the animal sniffing said filter.

In another advantageous implementation of the invention, traces of solid particles of substance to be detected retained on said filter are detected by chemical analysis equipment capable of detecting at least one chemical component of said substance to be detected.

In a particularly advantageous variant implementation of the invention, detection is performed of substance to be detected containing an explosive, for example an explosive selected from the group consisting in plastrite, hexogen, dynamite, PETN, TNT, "watergel", and mixtures thereof.

In another advantageous variant implementation of the method of the invention, detection is performed of a narcotic, for example selected from the group consisting in heroin, cocaine, Ecstasy, cannabis, marijuana, hashish, and mixtures thereof.

In another particularly advantageous implementation of the method of the invention, the filter comprises a woven or non-woven fabric presenting pore or mesh diameter adapted to filtering solid particles of said substance to be detected dispersed in air, for example a fabric of plastics material such as polyvinyl chloride (PVC), polyethylene, polypropylene and mixtures thereof.

In a particular variant implementation, the above-mentioned substance to be detected is in powder form, i.e. in the form of solid particles that are generally of a size that is sufficiently fine to make it inevitable that they will become dispersed in air, in particular during transport.

In a second aspect, the present invention also provides an apparatus for detecting a substance to be detected, containing at least one component that is dispersible in air in the form of solid particles, such as an explosive or a narcotic, such as heroin, cocaine, etc., the apparatus comprising:

a) optionally a substantially hermetically closed wrapping in which a load that might contain said substance to be detected can be placed at least for a predetermined storage time for allowing solid particles of said substance to disperse in air;

b) at least one sampling member for sampling the air contained in said closed space, the sampling member comprising at least one filter presenting pore or mesh size adapted to filtering solid particles of said substance to be detected that might be dispersed in the air contained in said closed space; and c) at least one pump for sucking in the air contained in said closed space via said sampling member containing said filter.

In an advantageous embodiment, at least one receptacle is also provided that is suitable for being hermetically closed for the purpose of storing at least temporarily the filter that might contain solid particles of said substance to be detected.

In an advantageous embodiment of the invention, said apparatus comprises a device comprising a plurality of supports for exposing to ambient air one or more filters that might contain solid particles of the substance to be detected, each of the supports optionally being provided with a filter that has been used in a different confined space to detect solid particles of the substance to be detected that might be contained in different loads. For example, the device may have six supports for exposing six filters that are disposed at predetermined distances from one another in ambient air.

In an advantageous embodiment of the apparatus of the invention, said apparatus comprises at least one analysis device for detecting the presence of solid particles of substance to be detected filtered or retained on the filter, for example a gas phase chromatographic apparatus, a nuclear magnetic resonance apparatus, in particular of the $^{13}C$ type, a mass spectrometer apparatus, and combinations thereof, such apparatuses being adapted to detect at least one air dispersible component of said substance to be detected contained in said dispersed solid particles.

In another advantageous embodiment of the invention, the above-mentioned filter has pore or mesh size adapted to detecting explosives, in particular explosives selected from the group consisting in plastrite, hexogen, dynamite, and pentrite, TNT, or "watergel".

In another advantageous embodiment of the invention, the filter has pore or mesh size adapted to detecting a narcotic, for example selected from the group consisting in heroin, cocaine, Ecstasy, cannabis, marijuana, hashish.

In another particular embodiment of the filter, it may comprise a hollow tubular outer casing containing a filter-forming element which may be supported, for example on a central element. This filter may comprise a filter-forming element proper such as woven or non-woven fabric possibly made of a plastics material, for example, such as polyvinyl chloride (PVC), polyethylene, polypropylene, and mixtures thereof.

In a particularly advantageous variant embodiment, the filter is provided at a length that is sufficient to project outside the tubular outer casing, said filter possibly also being suitable for mounting at the free and of the sampling member.

It will thus be understood that the invention makes it possible to detect said substance to be detected in a manner that is safe and reliable, reproducible, and fast, and without limitation on the number of loads for inspection that might contain said substance, and regardless of whether it is placed on pallets, in containers, on trucks or rail cars, or hidden on people passing through a transit hall or a waiting room, for example in a station or an airport, or indeed at a sea port.

By means of the invention, a filter gathers solid particles of substance to be detected that might be present in the loads to be inspected.

These particles can be analyzed for detection purposes either by using a biosensor device adapted to detecting solid particles of substance to be detected that is well known to the person skilled in the art, for example an automatic biosensor analysis device such as a nuclear magnetic resonance (NMR) device, e.g. for detecting $^{13}C$, or by a mass spectrometer device, also well known to the person skilled in the art.

In another variant embodiment, the biosensor detection can also be implemented by means of an animal such as a dog whose sense of smell has been specially trained to detect the substance to be detected such as explosives or narcotics.

It will thus be understood that the invention makes it possible to solve the above-specified technical problems, thereby improving public safety and combating more effectively against traffickers of narcotics.

BRIEF DESCRIPTION OF THE DRAWINGS

Other objects, characteristics, and advantages of the invention appear clearly in the light of the following explanatory description made with reference to accompanying FIGS. 1 to 10 which show a presently-preferred embodiment of apparatus of the invention enabling the detection method of the invention to be implemented.

It should be observed that FIGS. 1 to 10 form an integral part of the invention and thus contribute to the description in non-dissociable manner. Any technical characteristic which appears novel from the description read in the light of the drawings, compared with any state of the art is claimed as such and in its general means and its general function.

MORE DETAILED DESCRIPTION

Figure 1:
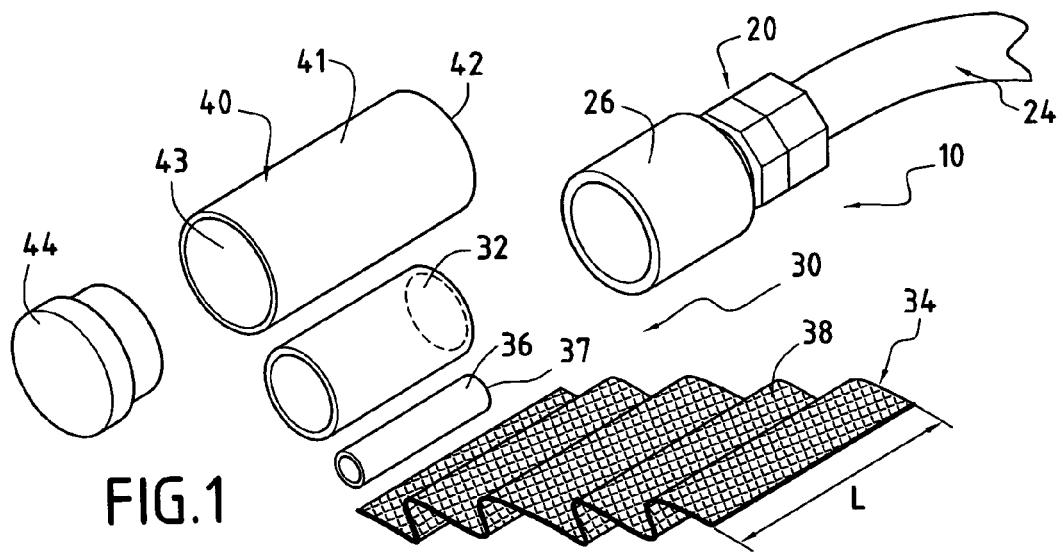
With reference to FIG. 1, there can be seen an exploded diagrammatic view of an air sampling member comprising at least one filter together with a receptacle for storing said filter in a manner that is essentially hermetic.

With reference to FIG. 1, apparatus of the invention is given overall reference number 10 and is designed for detecting a substance containing at least one component that is dispersible in air in the form of solid particles, such as explosives or narcotics, such as heroin, cocaine, etc. FIG. 1 shows only the essential means of the apparatus for performing such detection.

Thus, the apparatus 10 comprises at least one sampling member given overall reference number 20 serving to sample the air contained in a space 50 that is substantially hermetically closed as explained in detail below with reference to FIGS. 4 to 7 and 9 and 10. The sampling member 20 comprises at least one filter represented by overall reference number 30, said filter 30 presenting a pore or mesh size that is adapted to filtering solid particles of the substance to be detected that might be dispersed in the air contained in the closed space, as explained below.

In the context of the invention, the filter 30 is placed at a free end 22 of the sampling member 20 which essentially comprises an air suction hose 24 having a hollow cylindrical element 26 at one end for receiving the filter 30 and secured at said end 22 of the hose 24 by coupling means 28 such as a nut system, which system is well known to the person skilled in the art.

Figure 2:
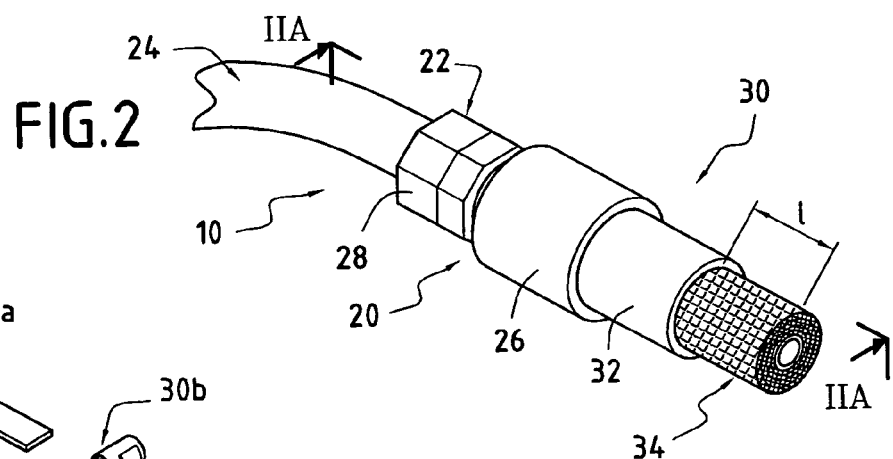
FIG. 2 shows the sampling member in the assembled state with the filter in place, one end of the filter projecting out from a hollow outer tubular case for receiving the filter.
Figure 2A:
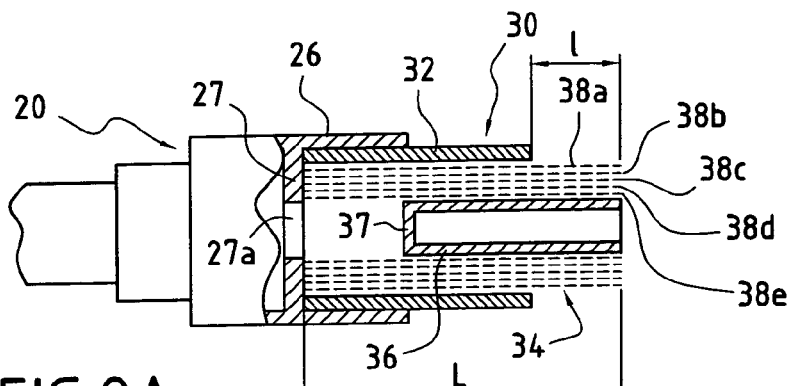
FIG. 2A is a longitudinal axial section on line 2A-2A of FIG. 2.
Figure 4:
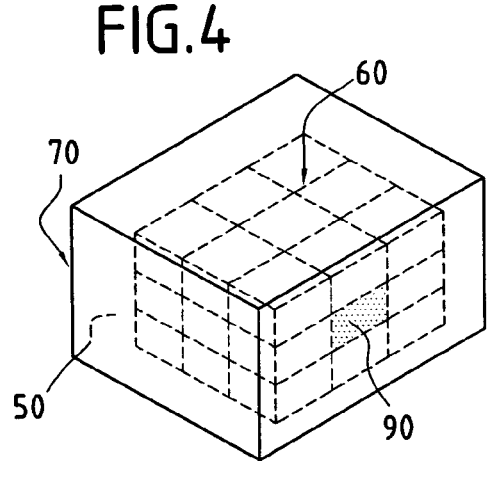
FIG. 4 is a diagram showing a load made up of a plurality of corresponding receptacles, containers, or packets shown in dashed lines, one of which, shown shaded, is suspect, the entire load being located inside premises.
Figure 5:
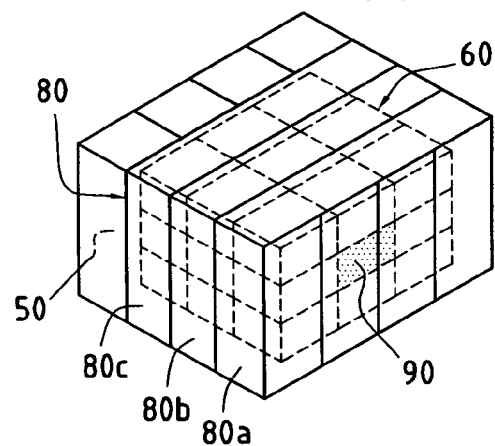
FIG. 5 is a diagram of the FIG. 4 load wrapped in plastic wrapping that is substantially hermetically closed.

In a presently-preferred embodiment of the invention, the filter 30 comprises a hollow tubular outer casing 32 that is clearly visible in FIGS. 1, 2, and 2A, containing a filter-forming element 34 proper which may, for example, be supported on a central element 36 that is likewise in the form of a hollow tube but that is closed at one end 37 so as to prevent air from passing through, and thus obliges air to pass through the filter-forming element 34, as can readily be understood on observing FIGS. 1, 2, and 2A.

In the presently preferred embodiment, the filter-forming element 34 comprises a woven or non-woven fabric 38 presenting pores or a mesh of size adapted to filtering solid particles of the above-specified substance that are dispersed in air, for example a fabric of a plastics material such as PVC, polyethylene, or polypropylene, and mixtures thereof. The pore or mesh size is not critical since the filtering or trapping of the solid particles of substance takes place because the filter-forming element 34 is obtained by rolling up the fabric 38 so as to define a plurality of layers 38a, 38b, 38c, 38d, 38e, for example, as can clearly be seen in FIG. 2A, with the consequence of this relatively tight winding between the layers of the rolled-up fabric 38 being that solid particles of the substance dispersed in air are filtered efficiently.

In a particular embodiment, the pore or mesh size is about 1 millimeter (mm) to about 2 mm in diameter or side, where the mesh can be made, for example, by horizontal and vertical weaving defining a substantially square-shape mesh, which square shape can be seen in FIGS. 1 and 2, and with the invention naturally not being limited to this particular shape.

Still in the presently preferred embodiment, the filter-forming element 34 is provided with a length L in the long direction of the fabric 38 for rolling up, see FIG. 1, that is long enough to enable a length l to project outside the tubular outer casing 32. It can be seen that the element 26 for receiving the filter-forming device 30 has a transverse partition 27 provided with a central orifice 27a for passing air. The transverse partition 27 serves to stop further insertion of the outer casing 32 of the filter-forming device 30 and also to hold the filter-forming element 34 in place which in this case is constituted by a fabric 38 which is rolled up so as to form a plurality of layers or turns 38a to 38e.

Naturally, the apparatus of the invention also comprises at least one pump (not shown) serving to suck in the air contained in the closed space 50 shown in FIGS. 4 to 7, as explained below with reference to those figures.

As also shown in FIG. 1, in an advantageous embodiment of the invention, at least one receptacle 40 is also provided, e.g. in the form of a tube 41 that is closed at one end 42 and open at its other end 43 for insertion of the filter-forming device 30 and which is capable of being hermetically closed by a closure element 44 such as a cap.

Figure 3:
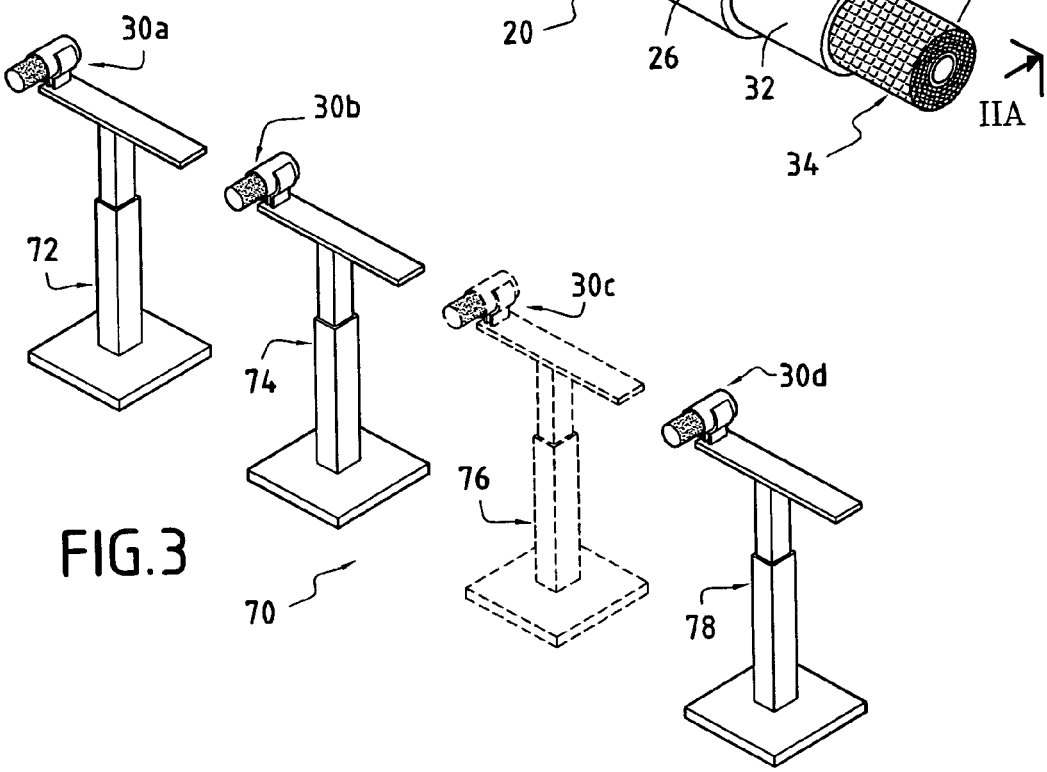
FIG. 3 shows a device comprising a plurality of supports for exposing a filter of the invention to ambient air.

FIG. 3 shows an advantageous embodiment of apparatus of the invention in which the apparatus further comprises a device 70 comprising a plurality of exposure supports 72, 74, 76, 78 so as to expose filter-forming devices 30a, 30b, 30c, 30d that might contain solid particles of the substance to be detected to ambient air. FIG. 3 shows a support device 76 which supports a filter-forming device, in this case 30c which is a genuine detector, while the other filter-forming devices 30a, 30b, and 30d serve as reference devices or as decoys. Nevertheless, each of the supports 72, 74, 76, 78 could possibly be supporting a filter-forming device 30 that has been used for inspecting different confinement spaces such as 50 in order to detect solid particles of substance to be detected that might be contained in different loads such as the load 60 shown in FIGS. 4 to 7. The load 60 may either be placed in a closed confinement space such as a storage room 70, or else when the load 60 is not contained in a closed space, said load 60 can itself be placed in a closed space, for example by placing it in wrapping 80 that is substantially hermetically closed and which can be formed by winding successive layers 80a, 80b, etc., of wrapping material from a roll.

Figure 6:
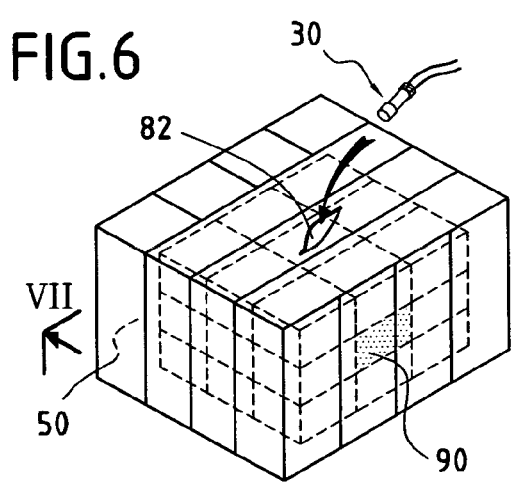
FIG. 6 shows a small opening being made through the substantially hermetically closed wrapping so as to enable the end of a sampling member of the invention to be inserted.
Figure 7:
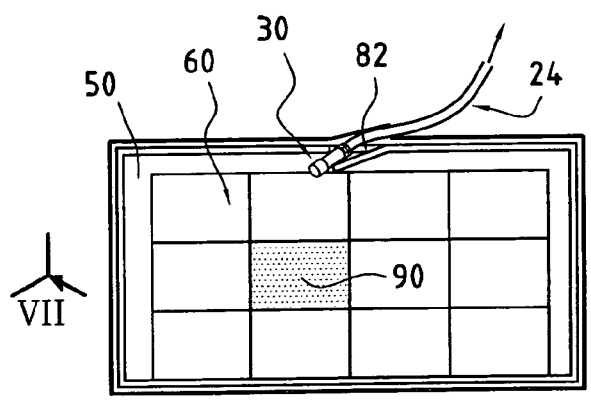
FIG. 7 is a diagrammatic section view on line 7-7 of FIG. 6 showing the end of the sampling member inserted inside the confined space defined by the substantially hermetically closed wrapping on the pallet of FIG. 6.

In FIGS. 6 and 7, it can be seen that air can be sampled by the sampling member 20 being inserted into the closed space such as 60 through an opening 82 into which the sampling member 20 is inserted in such a manner that the filter-forming device 30 penetrates into the inside of the confined space 50 in order to suck in air contained therein.

Figure 8:
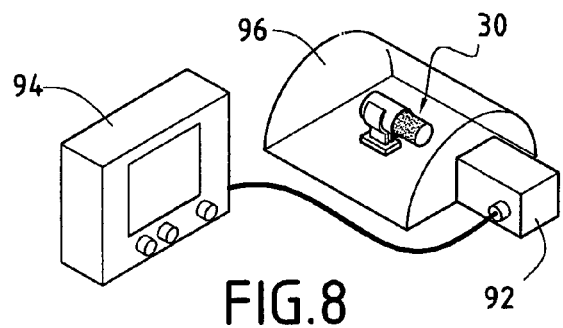
FIG. 8 is a diagram showing the step of analyzing or detecting particles of substance to be detected that might be present on the filter of the sampling member.

FIG. 8 shows the filter-forming device 30 placed inside an enclosure 96 in order to be subjected to analysis by an analysis device represented, for example, by a detector element 92 connected to a device 94 for displaying the results of the analysis. The analysis device 92, 94 is adapted to detecting traces of solid particles of the substance to be detected. This substance to be detected is advantageously present in the form of powder, i.e. in the form of solid particles, generally of a size that is sufficiently fine to make it almost inevitable that they become dispersed in air, particularly during transport.

In the invention, it is also preferred to detect substance in powder form such as explosive for obvious safety reasons, said explosive being one of those specified above, for example, or else to detect narcotics likewise for the obvious purposes of combating trafficking in narcotics, and said narcotics likewise being of the kind specified above, for example.

Figure 9:
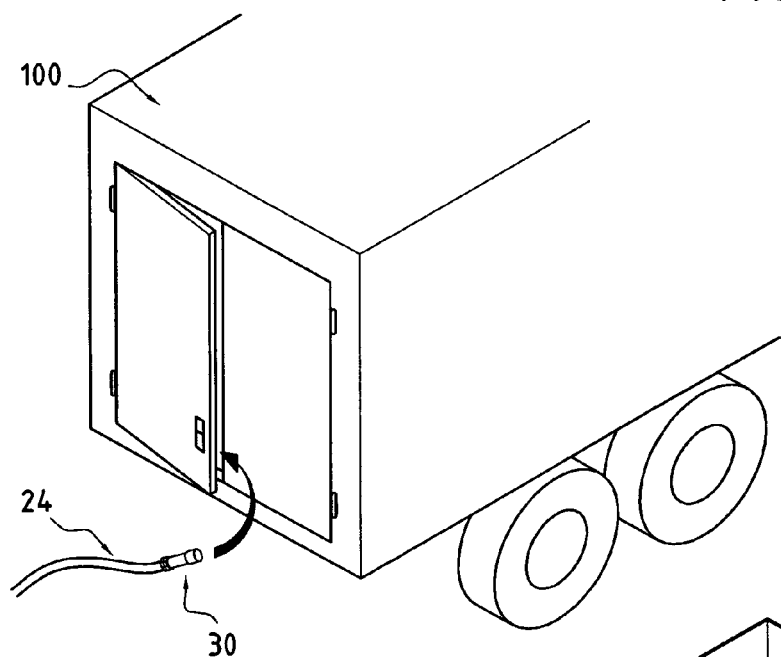
FIG. 9 is a diagram showing the sampling member of the invention being used to take a sample by opening ajar a door of transport means such as a truck containing loads that are to be inspected inside.

FIG. 9 shows transport means such as a truck 100 or a rail car capable of containing a multitude of loads of the same type as the load 60, any one of which might contain a suspect packet or parcel 90 containing a substance to be detected such as an explosive or a narcotic.

Figure 10:
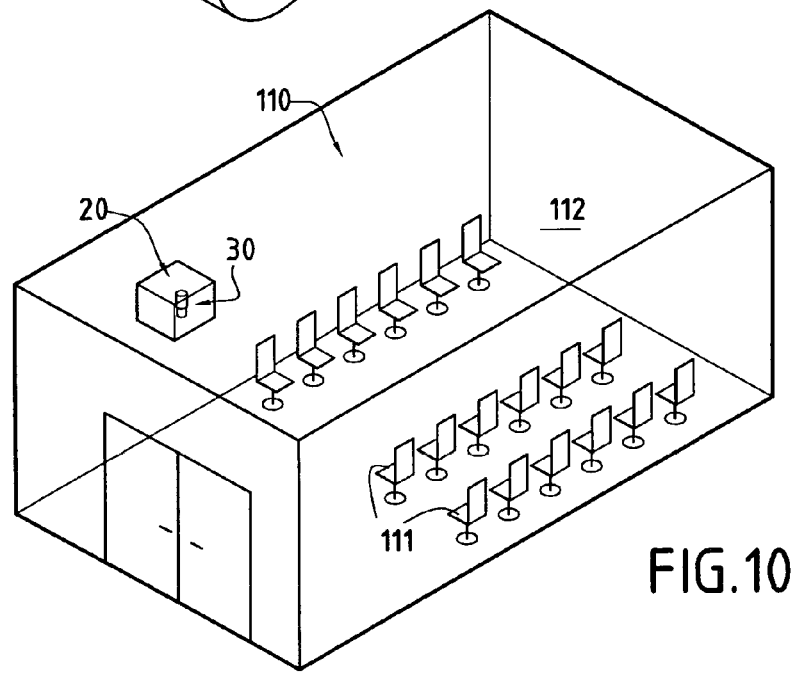
FIG. 10 shows a passenger embarkation or transit hall in a rail station or a port and including a sampling member of the present invention.

Finally, with reference to FIG. 10, there can be seen a diagram of a embarkation or transit hall 110 which is substantially hermetically closed and in which a certain number of passenger seats 111 are shown diagrammatically, said hall being fitted with at least one sampling member 20 having at least one filter-forming device 30 of the type described with reference to FIGS. 1, 2, and 2A and which serves, by sucking in the air contained in the confined space 112 inside the hall 110, to filter solid particles of substance to be detected that might be being transported by a passenger.

It will be understood that the invention serves equally well to implement the above-defined detection method and to solve the above-specified technical problem.

The invention is described below with the help of two examples one serving to detect substance to be detected that is in solid powder form such as an explosive (example 1) or a narcotic (example 2).

EXAMPLE 1

Preferred Example of Detecting Solid Substance to be Detected in Powder Form Such as an Explosive With the apparatus of the invention as described above with reference to FIGS. 1 to 3 and 8, in a first variant, the sampling member 20 is placed inside a pallet 60 wrapped in plastics wrapping 80 that is substantially hermetically closed, the sampling member including the filter 30 of the invention with pore or mesh size adapted to filtering solid particles of said substance to be detected that are dispersible in air, said sampling member 30 penetrating inside the confined space 50 defined by said pallet and the substantially hermetic wrapping 80. The pump is put into operation for a predetermined length of time, generally of the order of 3 minutes (min) to 10 min, in order to suck in the air present in the space 50 defined by the wrapping 80 covering the pallet 60, thereby gathering any solid particles dispersed in the air of the substance to be detected that might be present inside said pallet, for example, in this case, in the packet or parcel 90 that is identified by shading in FIGS. 4 to 7.

The filter 30 is withdrawn and placed immediately inside a receptacle 40 for at least temporary storage of said filter 30, which receptacle is closed hermetically using the leaktight closure element 44.

Thereafter, any particles of substance to be detected that might be present on said filter are analyzed or detected, for example by means of a biosensor analysis device such as 70 (FIG. 3), or 92, 94 of FIG. 8 adapted to detecting particles of said substance to be detected, in this case, for example, an explosive such as plastrite, hexogen, dynamite, PETN, TNT, or "watergel". The analysis device may comprise one or more supports such as 72 to 78 for placing the filter in ambient air for biosensing detection by means of an animal such as a dog whose sense of smell has been specially trained to detecting the substance to be detected, such as an explosive or a narcotic, or in a different variant embodiment, an automatic biosensor analysis device, for example a nuclear magnetic resonance device for detecting $^{13}C$ for example, or by a mass spectrometer device, etc. as are well known to the person skilled in the art. A particularly suitable apparatus is sold under the trademark IONSCAN by the German supplier Barringer®, and is capable of detecting traces of parts per million (ppm) order of said substance to be detected, for example an explosive.

In the context of the invention, the flow rate of the pump is not critical. For example, it is possible to use a pump which sucks in air at a rate of about 120 liters per minute (l/min).

EXAMPLE 2 OF THE INVENTION

Detecting Solid Substance in Powder Form Such as a Narcotic

The procedure is the same as in example 1, and the same filter is used which likewise needs to present pore or mesh size adapted to detecting the narcotic.

In this example, detection can be performed equally well on a pallet placed in storage premises, or on a truck 100 containing a plurality of said pallets. With a truck 100, the pallets are generally wrapped individually, but if not, the truck itself defines a confined space that is substantially hermetically closed.

In this case, the analysis device is designed to search for a particular type of substance to be detected, for example, in this case, a narcotic. The narcotic is generally heroin, cocaine, Ecstasy, cannabis, marijuana, hashish, as is well known to the person skilled in the art.

What is claimed is:

1. A method of detecting a substance to be detected containing at least one component dispersible in air in the form of solid particles, comprising the following steps:
    a) when a load that might contain said substance to be detected is not itself contained in a closed space, placing said load in a substantially closed space, at least for a predetermined storage time for allowing solid particles of said substance to be detected to disperse in air;
    b) inserting at least one sampling member for sampling the air contained inside said closed space, at least after said load has been stored for said predetermined time in said closed space, said sampling member comprising at least one filter presenting pore or mesh size adapted to filtering solid particles of said substance that might be dispersed in the air contained in said closed space;
    said filter comprising a hollow tubular outer casing containing a filter-forming element which is supported on a central element that is likewise in the form of a hollow tube but that is closed at one end so as to prevent air from passing through and to oblige air to pass longitudinally through substantially the full length of the filter-forming element;
    said filter-forming element comprising a woven or non-woven fabric;
    c) sucking in the air contained in said closed space via said sampling member containing said filter for a period of time necessary for filtering a sufficient quantity of air that might contain solid particles of said substance dispersed in said air;
    d) removing the filter from the sampling member and optionally placing it in a hermetically closed receptacle prior to performing detection; and
    e) proceeding to detect the presence, if any, of a solid particles of substance to be detected retained on said filter, at room temperature.

2. The method of claim 1, wherein solid particles of substance to be detected present on said filter are detected by performing analysis in an analysis device adapted to detect traces of solid particles of said substance to be detected.

3. The method of claim 1, wherein the presence, if any, of traces of substance to be detected is detected with the help of a biosensor device.

4. The method of claim 3, wherein said substance has a smell, comprising detecting the smell of traces of solid particles of substance to be detected retained on said filter, by an animal sniffing said filter.

5. The method of claim 1, wherein traces of solid particles of substance to be detected retained on said filter are detected by chemical analysis equipment capable of detecting at least one chemical component of said substance to be detected.

6. The method of claim 1, wherein detection is performed of said substance to be detected containing an explosive.

7. The method of claim 6, wherein said explosive is selected from the group consisting of plastrite, hexogen, dynamite, PETN, TNT, "watergel", and mixtures thereof.

8. The method of claim 1, wherein detection is performed of a narcotic.

9. The method of claim 7, wherein said narcotic is selected from the group consisting of heroin, cocaine, Ecstasy, cannabis, marijuana, hashish, and mixtures thereof.

10. The method of claim 1, wherein the filter-forming element comprises a fabric presenting pore or mesh diameter adapted to filtering solid particles of said substance to be detected dispersed in air.

11. The method of claim 10, wherein said fabric is a fabric of plastics material.

12. The method of claim 10, wherein said fabric is a fabric of plastics material selected from the group consisting of polyvinyl chloride, polyethylene, polypropylene and mixtures thereof.

13. The method of claim 11, wherein said fabric is a woven fabric.

14. The method of claim 11, wherein said fabric is a non-woven fabric.

15. The method of claim 1, wherein said step of placing said load in a substantially closed space comprises placing said load in a wrapping that is substantially hermetically closed.

16. A method of detecting a substance to be detected containing at least one component dispersible in air in the form of solid particles, comprising the following steps:
   a) when a load that might contain said substance to be detected is not itself contained in a closed space, placing said load in a substantially closed space, at least for a predetermined storage time for allowing solid particles of said substance to be detected to disperse in air;
   b) inserting at least one sampling member for sampling the air contained inside said closed space, at least after said load has been stored for said predetermined time in said closed space, said sampling member comprising at least one filter presenting pore or mesh size adapted to filtering solid particles of said substance that might be dispersed in the air contained in said closed space;
   said filter comprising a hollow tubular outer casing containing a filter-forming element which is supported on a central element that is likewise in the form of a hollow tube but that is closed at one end so as to prevent air from passing through and to oblige the air to pass longitudinally through substantially the full length of the filter-forming element, said filter-forming element comprising a woven or non-woven fabric;
   c) sucking in the air contained in said closed space via said sampling member containing said filter for a period of time necessary for filtering a sufficient quantity of air that might contain solid particles of said substance dispersed in said air;
   d) removing the filter from the sampling member and optionally placing it in a hermetically closed receptacle prior to performing detection; and
   e) proceeding with the help of a biosensor device to detect the presence, if any, of solid particles of substance to be detected retained on said filter, at room temperature.

17. A method of detecting a substance to be detected containing at least one component dispersible in air in the form of solid particles, comprising the following steps:
   a) when a load that might contain said substance to be detected is not itself contained in a closed space, placing said load in a substantially closed space, at least for a predetermined storage time for allowing solid particles of said substance to be detected to disperse in air;
   b) inserting at least one sampling member for sampling the air contained inside said closed space, at least after said load has been stored for said predetermined time in said closed space, said sampling member comprising at least one filter presenting pore or mesh size adapted to filtering solid particles of said substance that might be dispersed in the air contained in said closed space;
   said filter comprising a hollow tubular outer casing containing a filter-forming element which is supported on a central element that is likewise in the form of a hollow tube but that is closed at one end so as to prevent air from passing through and to oblige air to pass longitudinally through substantially the full length of the filter-forming element;
   said filter-forming element comprising a woven or non-woven fabric;
   c) sucking in the air contained in said closed space via said sampling member containing said filter for a period of time necessary for filtering a sufficient quantity of air that might contain solid particles of said substance dispersed in said air;
   d) removing the filter from the sampling member and optionally placing it in a hermetically closed receptacle prior to performing detection; and
   e) proceeding to detect the presence, if any, of solid particles of substance to be detected retained on said filter, and
   wherein said substance has a smell, said detecting step e) comprising detecting the smell of traces of solid particles of said substance to be detected retained on said filter, by an animal sniffing said filter.

* * * * *